(12) United States Patent
Meridew

(10) Patent No.: US 7,976,565 B1
(45) Date of Patent: Jul. 12, 2011

(54) EXPANDING SUTURE ANCHOR HAVING AN ACTUATOR PIN

(75) Inventor: Jason D Meridew, Syracuse, IN (US)

(73) Assignee: Biomet Sports Medicine, LLC, Warsaw, IN (US)

(*) Notice: Subject to any disclaimer, the term of this patent is extended or adjusted under 35 U.S.C. 154(b) by 1237 days.

(21) Appl. No.: 11/006,398

(22) Filed: Dec. 7, 2004

(51) Int. Cl.
*A61F 2/08* (2006.01)
(52) U.S. Cl. .......................................... 606/232; 606/1
(58) Field of Classification Search .................. 606/72, 606/232
See application file for complete search history.

(56) References Cited

U.S. PATENT DOCUMENTS

| | | | | |
|---|---|---|---|---|
| 3,708,883 A | * | 1/1973 | Flander | 433/174 |
| 4,409,974 A | | 10/1983 | Freedland | |
| 4,653,489 A | | 3/1987 | Tronzo | |
| 4,738,255 A | | 4/1988 | Goble et al. | |
| 5,013,316 A | | 5/1991 | Goble et al. | |
| 5,087,199 A | * | 2/1992 | Lazarof | 433/173 |
| 5,167,665 A | | 12/1992 | McKinney | |
| 5,258,016 A | | 11/1993 | DiPoto et al. | |
| 5,268,001 A | * | 12/1993 | Nicholson et al. | 606/232 |
| 5,326,205 A | * | 7/1994 | Anspach et al. | 411/43 |
| 5,464,427 A | | 11/1995 | Curtis et al. | |
| 5,472,452 A | * | 12/1995 | Trott | 606/232 |
| 5,474,572 A | | 12/1995 | Hayhurst | |
| 5,480,403 A | * | 1/1996 | Lee et al. | 606/232 |
| 5,486,197 A | * | 1/1996 | Le et al. | 606/232 |
| 5,501,695 A | * | 3/1996 | Anspach et al. | 606/232 |
| 5,531,792 A | | 7/1996 | Huene | |
| 5,584,835 A | * | 12/1996 | Greenfield | 606/232 |
| 5,601,558 A | | 2/1997 | Torrie et al. | |
| 5,643,321 A | * | 7/1997 | McDevitt | 606/232 |
| 5,645,589 A | | 7/1997 | Li | |
| 5,649,963 A | | 7/1997 | McDevitt | |
| 5,665,110 A | | 9/1997 | Chervitz et al. | |
| 5,713,903 A | | 2/1998 | Sander et al. | |
| 5,720,753 A | | 2/1998 | Sander et al. | |
| 5,725,529 A | | 3/1998 | Nicholson et al. | |
| 5,725,541 A | | 3/1998 | Anspach, III et al. | |
| 5,741,282 A | | 4/1998 | Anspach, III et al. | |
| 5,814,071 A | | 9/1998 | McDevitt et al. | |
| 5,911,721 A | | 6/1999 | Nicholson et al. | |
| 5,928,244 A | | 7/1999 | Tovey et al. | |
| 5,931,844 A | * | 8/1999 | Thompson et al. | 606/144 |
| 5,935,129 A | * | 8/1999 | McDevitt et al. | 606/232 |
| 5,941,901 A | | 8/1999 | Egan | |
| 5,968,044 A | | 10/1999 | Nicholson et al. | |
| 6,048,343 A | | 4/2000 | Mathis et al. | |
| 6,056,751 A | | 5/2000 | Fenton, Jr. | |
| 6,129,762 A | | 10/2000 | Li | |

(Continued)

OTHER PUBLICATIONS

Cannulated ArthroRivet™ Anchor brochure, Arthrotek® Aug. 2003.

(Continued)

*Primary Examiner* — Darwin P Erezo
*Assistant Examiner* — Mark Mashack
(74) *Attorney, Agent, or Firm* — Harness, Dickey

(57) ABSTRACT

A method and apparatus for reattaching soft tissue to a preselected boney structure using an expanding suture anchor. Generally, an expanding suture anchor having an actuator pin is provided to fully secure a suture into the boney structure. The actuator pin is molded to a portion of the suture anchor and detaches from the suture anchor when the suture anchor is fully engaged with the boney structure. Thus, the soft tissue is fully secured to the boney structure ensuring proper healing.

34 Claims, 7 Drawing Sheets

U.S. PATENT DOCUMENTS

| | | | |
|---|---|---|---|
| 6,149,669 A | 11/2000 | Li | |
| 6,210,376 B1 | 4/2001 | Grayson | |
| 6,214,012 B1 | 4/2001 | Karpman et al. | |
| 6,227,860 B1* | 5/2001 | Hobo | 433/173 |
| 6,315,787 B1* | 11/2001 | Tsugita et al. | 606/213 |
| 6,319,269 B1 | 11/2001 | Li | |
| 6,328,758 B1* | 12/2001 | Tornier et al. | 606/232 |
| 6,447,516 B1 | 9/2002 | Bonutti | |
| 6,464,706 B1 | 10/2002 | Winters | |
| 6,517,564 B1 | 2/2003 | Grafton et al. | |
| 6,524,316 B1 | 2/2003 | Nicholson et al. | |
| 6,527,794 B1* | 3/2003 | McDevitt et al. | 606/232 |
| 6,554,830 B1 | 4/2003 | Chappius | |
| 6,565,572 B2 | 5/2003 | Chappius | |
| 6,575,976 B2 | 6/2003 | Grafton | |
| 6,582,453 B1* | 6/2003 | Tran et al. | 606/232 |
| 6,599,295 B1 | 7/2003 | Tornier et al. | |
| 6,623,492 B1 | 9/2003 | Berube et al. | |
| 6,645,227 B2 | 11/2003 | Fallin et al. | |
| 6,652,561 B1 | 11/2003 | Tran | |
| 6,660,023 B2 | 12/2003 | McDevitt et al. | |
| 6,770,073 B2 | 8/2004 | McDevitt et al. | |
| 6,863,671 B1 | 3/2005 | Strobel et al. | |
| 6,994,725 B1 | 2/2006 | Goble | |
| 7,037,324 B2 | 5/2006 | Martinek | |
| 7,250,055 B1 | 7/2007 | Vanderwalle | |
| 7,572,283 B1* | 8/2009 | Meridew | 606/321 |
| 2001/0051807 A1 | 12/2001 | Grafton | |
| 2002/0095180 A1 | 7/2002 | West, Jr. et al. | |
| 2002/0111653 A1* | 8/2002 | Foerster | 606/232 |
| 2002/0128684 A1* | 9/2002 | Foerster | 606/232 |
| 2003/0144667 A1 | 7/2003 | Enayati | |
| 2003/0187444 A1* | 10/2003 | Overaker et al. | 606/72 |
| 2004/0133239 A1 | 7/2004 | Singhatat | |
| 2004/0138707 A1* | 7/2004 | Greenhalgh | 606/232 |
| 2004/0193167 A1 | 9/2004 | Tucciarone et al. | |
| 2004/0225292 A1 | 11/2004 | Sasso et al. | |
| 2004/0243179 A1* | 12/2004 | Foerster | 606/232 |
| 2004/0267265 A1 | 12/2004 | Kyle | |
| 2005/0015059 A1 | 1/2005 | Sweeney | |
| 2005/0075668 A1* | 4/2005 | Lizardi | 606/232 |
| 2005/0137707 A1 | 6/2005 | Malek | |
| 2006/0235413 A1 | 10/2006 | Denham et al. | |
| 2007/0112352 A1 | 5/2007 | Sorensen et al. | |
| 2007/0265704 A1 | 11/2007 | Mayer et al. | |
| 2008/0281325 A1 | 11/2008 | Stone et al. | |
| 2009/0299386 A1 | 12/2009 | Meridew | |

OTHER PUBLICATIONS

Cannulated ArthroRivet™, Arthrotek® Inventing the Future of Arthroscopy, print out of web site http://www.arthrotek.com/prodpage.cfm?c=0A05&p=0102 (printed Dec. 12, 2006) Copyright 2005, Arthrotek, Inc.

* cited by examiner

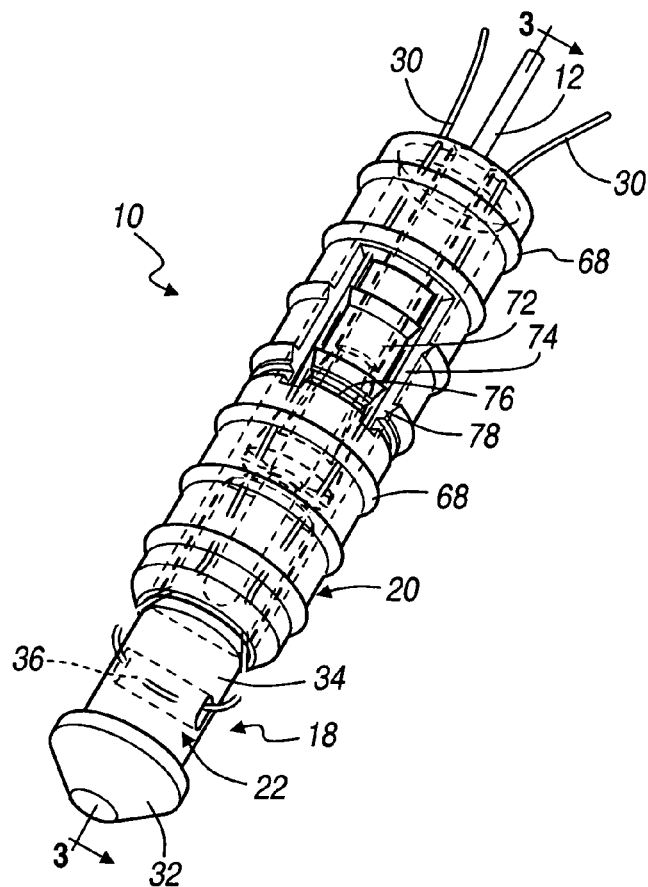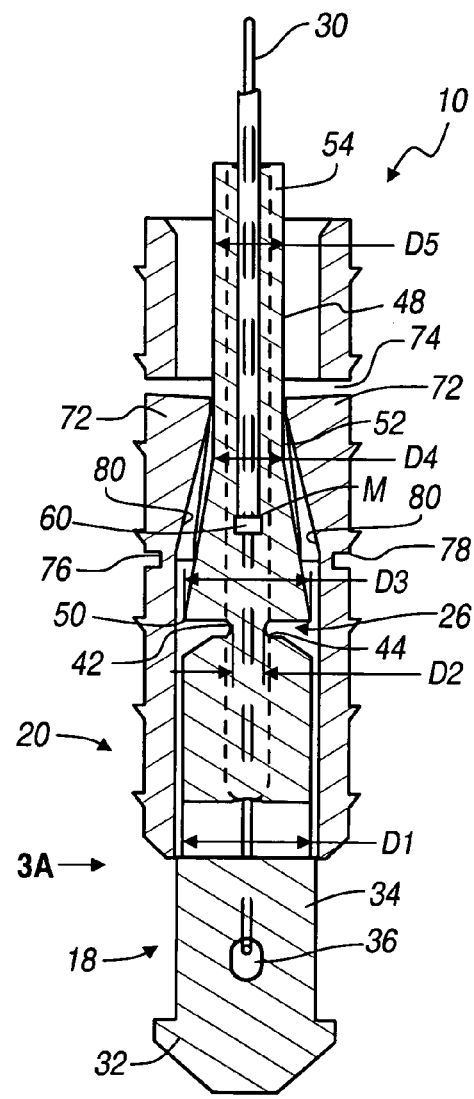
FIG. 1
FIG. 3
FIG. 3A

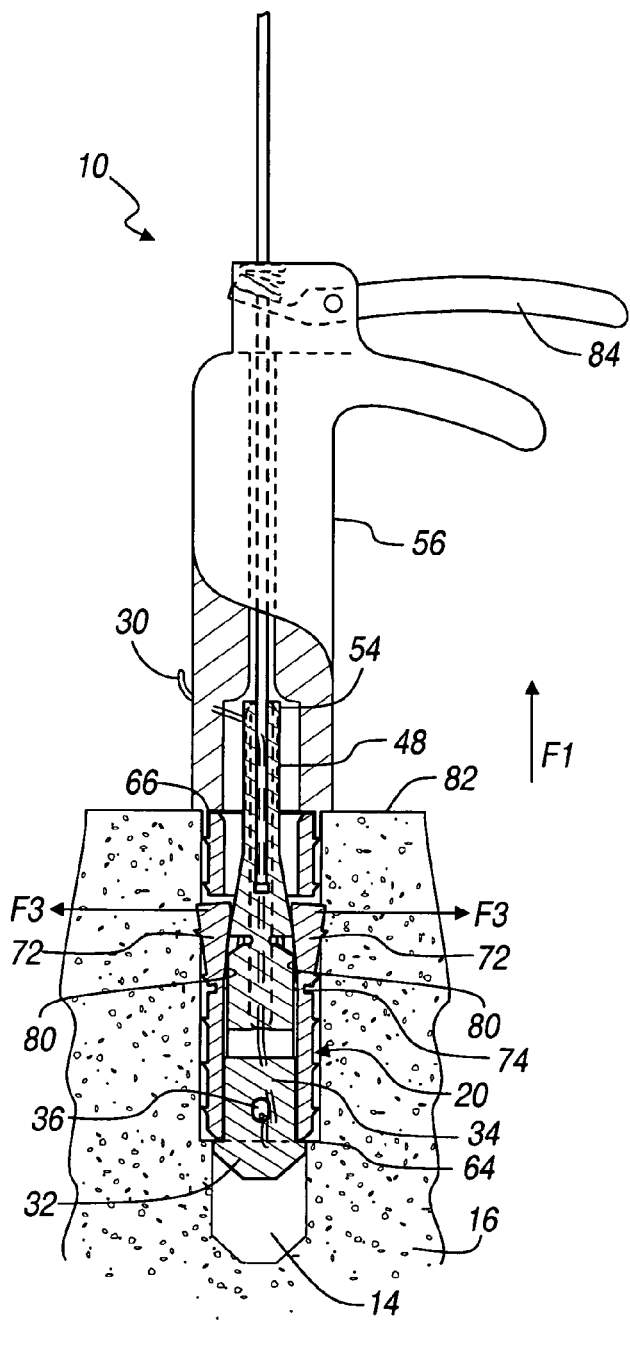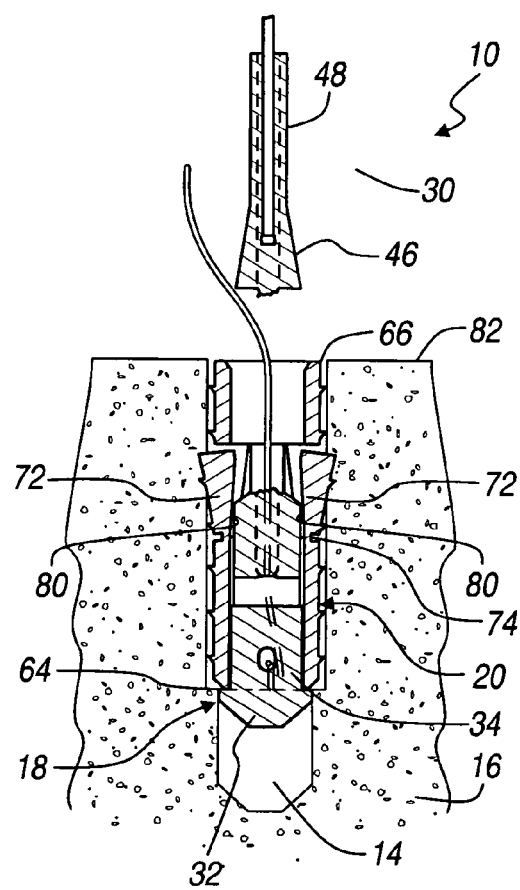
FIG. 4B
FIG. 4C

EXPANDING SUTURE ANCHOR HAVING AN ACTUATOR PIN

FIELD

The present invention relates generally to suture anchors, and particularly to a method and apparatus for an expanding suture anchor having an actuator pin.

BACKGROUND

Various procedures may be performed to repair soft tissue in the body. Generally, it is known to fix the soft tissue to a selected area on the bone by providing a suture through a selected portion of the soft tissue while securing the other end of the suture to the selected area on the bone using a suture anchor.

Suture anchors may be retained in the selected area of the bone via a feature of the suture anchor which expands when the suture is pulled by the surgeon. In hard bone, such as, for example, a femur, however, the suture anchor may not fully expand into the bone because the surgeon is not able to apply sufficient force to the suture. Thus, the suture may become loose in the boney structure which could lead to increased healing times or improper healing.

Accordingly, it would be desirable to provide an expanding suture anchor that will fully expand into a hard boney structure.

SUMMARY

A method and apparatus for reattaching soft tissue to a pre-selected boney structure using an expanding suture anchor. Generally, an expanding suture anchor having an actuator pin is provided to secure a suture into the boney structure. The actuator pin is attached to a portion of the suture anchor and detaches from the suture anchor when the suture anchor is engaged with the boney structure. Thus, the soft tissue is secured to the boney structure ensuring proper healing.

A suture anchor for attaching soft tissue to a pre-selected area of a boney structure that includes an insert operable to retain the soft tissue is provided. A sleeve is disposed around a portion of the insert. The sleeve is operable to engage the boney structure to retain the insert in the boney structure. An actuator pin is molded into the insert. The actuator pin is operable to engage the sleeve with the boney structure.

An expandable suture anchor for attaching a suture to a pre-selected area of a boney structure includes an insert operable to retain the suture is provided. The insert includes a breakaway portion. A sleeve is disposed around a portion of the insert including the breakaway portion. The sleeve is operable to engage the boney structure to retain the insert in the boney structure. An actuator pin is fixedly attached to the breakaway portion of the insert. The actuator pin is operable to cause the sleeve to fully engage the boney structure. The breakaway portion of the insert is detached from the insert upon the full engagement of the sleeve with the boney structure.

A method for attaching a soft tissue to a pre-selected area of a boney structure including forming a cavity in the boney structure for receipt of a suture anchor is also disclosed. After disposing the suture anchor in the cavity a retractive force is applied to the suture anchor. The retractive force causes a portion of the suture anchor to breakaway when the suture anchor is fully retained in the boney structure.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a perspective view of an expanding suture anchor having an actuator pin according to various embodiments;

FIG. 3 is a cross-sectional view taken along line 3-3 of FIG. 1;

FIG. 3A is a detailed view of FIG. 3;

FIG. 4B is an environmental view of the suture anchor as the retractive force is applied to move the suture anchor into the fully expanded position;

FIG. 4C is an environmental view illustrating the suture anchor in a fully expanded position;

DETAILED DESCRIPTION OF VARIOUS EMBODIMENTS

The following description of various embodiments is merely exemplary in nature and is in no way intended to limit the invention, its application, or uses. Although the following description is related generally to a suture anchor that can be positioned in a pre-drilled hole, that is a hole provided in a boney structure for acceptance of the suture anchor, it will be understood that a suture anchor including an impacting tip or self-drilling thread may be provided as well. Moreover, it will be understood that the suture anchor, as described and claimed herein, can be used with any appropriate surgical procedure. Therefore, it will be understood that the following discussions is not intended to limit the scope of the appended claims.

Figure 4A:
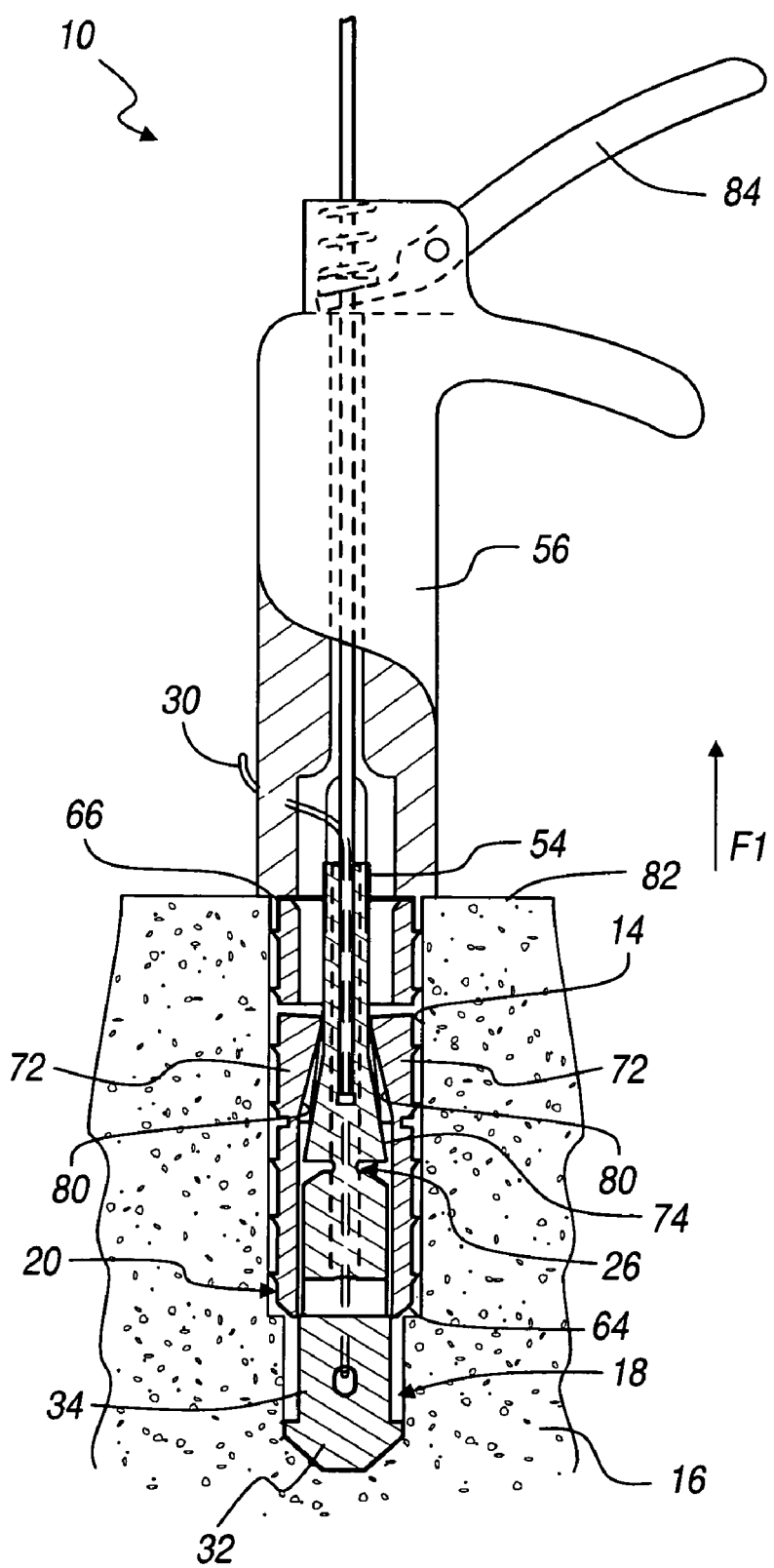
FIG. 4A is an environmental view of a use of the suture anchor shown in FIG. 1.

With reference to FIG. 1, an expanding suture anchor 10 having an actuator pin 12 is illustrated. The suture anchor 10 is operable in a first configuration for insertion into a pre-drilled hole 14 in a boney structure 16 (as shown in FIG. 4A) and operable in a second configuration to secure the suture anchor 10 in the pre-drilled hole 14 (as shown in FIG. 4C). The suture anchor 10 generally includes an insert 18 molded to the actuator pin 12 and partially disposed in a sleeve 20.

Figure 2:
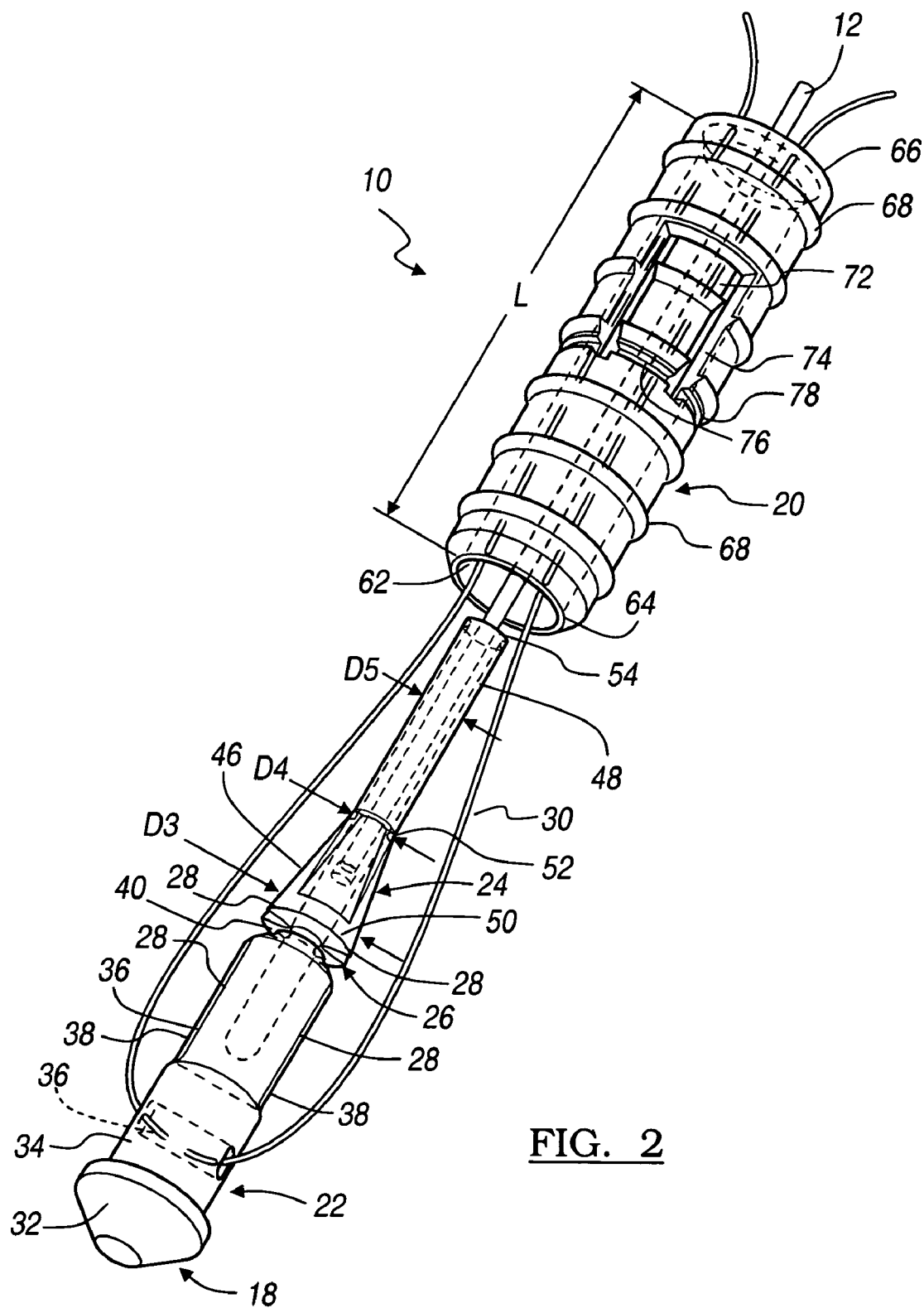
FIG. 2 is an exploded view of the suture anchor in FIG. 1.

With continuing reference to FIG. 1 and additional reference to FIGS. 2 and 3, the insert 18 includes a suture receiving portion 22 and an end section 24 displaced from the suture receiving portion 22 by a breakaway section 26. The suture receiving portion 22 and end section 24 have a tensile and torsion strength which are greater than the tensile and torsion strength of the breakaway section 26 such that the suture receiving portion 22 and end section 24 will be severed by the breakaway section 26 without damage to the structural integrity of either section. The insert 18 is generally insert molded from a resorbable material, such as, for example, Lactosorb® available from Biomet Inc. of Warsaw, Ind., however, it will be understood that other types of biocompatible materials and other methods of forming could be used.

At least one groove 28 extends throughout a length L1 of the suture receiving portion 22 and the end section 24 for receipt of strands from a suture 30 therein. The suture receiving portion 22 further has a tip 32 and a cylindrical body 34. The tip 32 is generally conical in shape, however, any other desired shape may be used. The cylindrical body 34 has a diameter D1 which is sized to ensure an interference fit with the sleeve 20 such that the cylindrical body 34 can slide within the sleeve 20. The cylindrical body 34 includes a formed eyelet 36 extending through the cylindrical body 34 to provide an attachment point for the suture 30, as shown in FIG. 3A. Referring back to FIG. 3, the cylindrical body 34 may further include a tapered section 40 leading to the breakaway section 26.

The breakaway section 26 has a diameter D2 which is generally one-half the size of the diameter D1 of the cylindrical body 34. The breakaway section 26 may include two necked portions 42, 44 which facilitate the fracturing of the breakaway section 26 by reducing the fracture strength of the breakaway section 26 in torsion and tension as compared to the suture receiving portion 22 and the end section 24. The diameter of the necked portions 42, 44 may vary to enable different fracture loads for various applications, but generally the force required to fracture the necked portions 42, 44 will be between 10-12 foot-pounds. The fracturing of the breakaway section 26 detaches the suture receiving portion 22 from the end section 24 of the insert 18 (as illustrated in FIG. 4C).

With continued reference to FIG. 3 and additional reference to FIG. 2, the end section 24 has a tapered portion 46 coupled to an annular body 48. The tapered portion 46 includes a first diameter D3 at a first end 50 which tapers to a second diameter D4 at a second end 52. In general, the first diameter D3 of the tapered portion 46 is approximately equal to the diameter D1 of the suture receiving portion 22. The tapered portion 46 operates to place the suture anchor 10 in the second position to engage the boney structure 16 as will be described in greater detail below. The second end 52 of the tapered portion 46 is coupled to the annular body 48. The annular body 48 is generally cylindrical and has a constant diameter D5. The diameter D5 of the annular body 48 may be larger than the second diameter D4 of the tapered portion 46 but yet smaller than the first diameter D3 of the tapered portion 46. The annular body 48 can extend beyond the sleeve 20 when the suture anchor 10 is assembled to provide a locator 54 for an actuator gun 56 (as shown in FIG. 4A) for the application of a retractive force F1, however, this is not necessary, as will be discussed further below. The annular body 48 and tapered portion 46 each further include a formed central bore 58 for receipt of the actuator pin 12 therein.

The actuator pin 12 is fixedly attached to the annular body 48 and tapered portion 46 via insert molding. In particular, the insert 18 is formed around the actuator pin 12, ensuring secure and precise attachment. The actuator pin 12 is positioned in the formed central bore 58 of the annular body 48 and tapered portion 46 such that the actuator pin 12 is removed from the suture anchor 10 when the breakaway section 26 is fractured. The actuator pin 12 can be made of any suitable biocompatible corrosive resistance material, such as, for example, surgical steel. In this regard, the actuator pin 12 need not be made of the same material as the sleeve 20.

The actuator pin 12 further includes a formed cavity 60 which retains the actuator pin 12 in the insert 18 through out the application of the retractive force F1. More specifically, as best shown in FIG. 3, as the insert 18 is formed around the actuator pin 12, material M is formed under the cavity 60. Thus, this material M must be displaced in order to remove the actuator pin 12 from the insert 18. Accordingly, the retractive force F1 must be less than the fracture strength of the material M to ensure the actuator pin 12 is retained in the insert 18. Similarly, the size of the cavity 60 can be modified to allow the accumulation of varying amounts of material M depending on the amount of retractive force F1 required to secure the suture anchor 10 in a given boney structure.

With continuing reference to FIGS. 2 and 3 and additional reference to FIG. 1, the sleeve 20 is disposed about a substantial portion of the insert 18. More specifically, the sleeve 20 includes a throughbore 62 for receipt of the insert 18 therein. The sleeve 20 has a length L which may be configured such that the suture receiving portion 22 and locator 54 are exposed when the suture anchor 10 is in the first position. For example, a first end 64 of sleeve 20 is shown covering the breakaway section 26 and approximately one half of the cylindrical body 34 of the suture receiving portion 22 and a second end 66 of the sleeve 20 covers the tapered portion 46 and approximately one half of the annular body 48 of the end section 24. The sleeve 20 is typically made from a resorbable material, such as, for example, Lactosorb®, however other suitable materials could be employed.

The sleeve 20 is generally cylindrical in nature, and may include at least one ring or securement device 68 on an external surface 70 of the sleeve 20. Although the sleeve 20 is shown having a ring 68, it is to be understood various other external features could be disposed on the sleeve 20 such as, for example, barbs or threads. The at least one ring 68 further aids in the engagement of the suture anchor 10 in the pre-drilled hole 14. The sleeve 20 also includes at least one expanding member 72 hingably coupled to the sleeve 20 to engage the pre-drilled hole 14. Specifically, the expanding member 72 is defined by a slot 74 formed in the sleeve 20 and includes a hinge 76. In one embodiment, the sleeve 20 includes two expanding members 72 located approximately 180 degrees apart. It shall be noted, however, that the expanding members 72 could be located at any position on the sleeve 20 which would engage the boney surface 16. The expanding members 72 are located at a midsection 78 of the sleeve 20. The expanding members 72 expand to lock into the boney structure 16 when the retractive force F1 is applied to the actuator pin 12 and in turn to a tapered interior bearing surface 80 on the expanding members 72.

With reference now to FIG. 4A, after the hole 14 has been drilled into the boney structure 16 and the eyelet 36 of the insert 18 has been threaded with the suture 30, the suture anchor 10 can be inserted into the pre-drilled hole 14 as shown. The suture anchor 10 is generally configured such that only the locator 54 of the end section 24 extends beyond a top surface 82 of the boney structure 16.

Figure 4D:
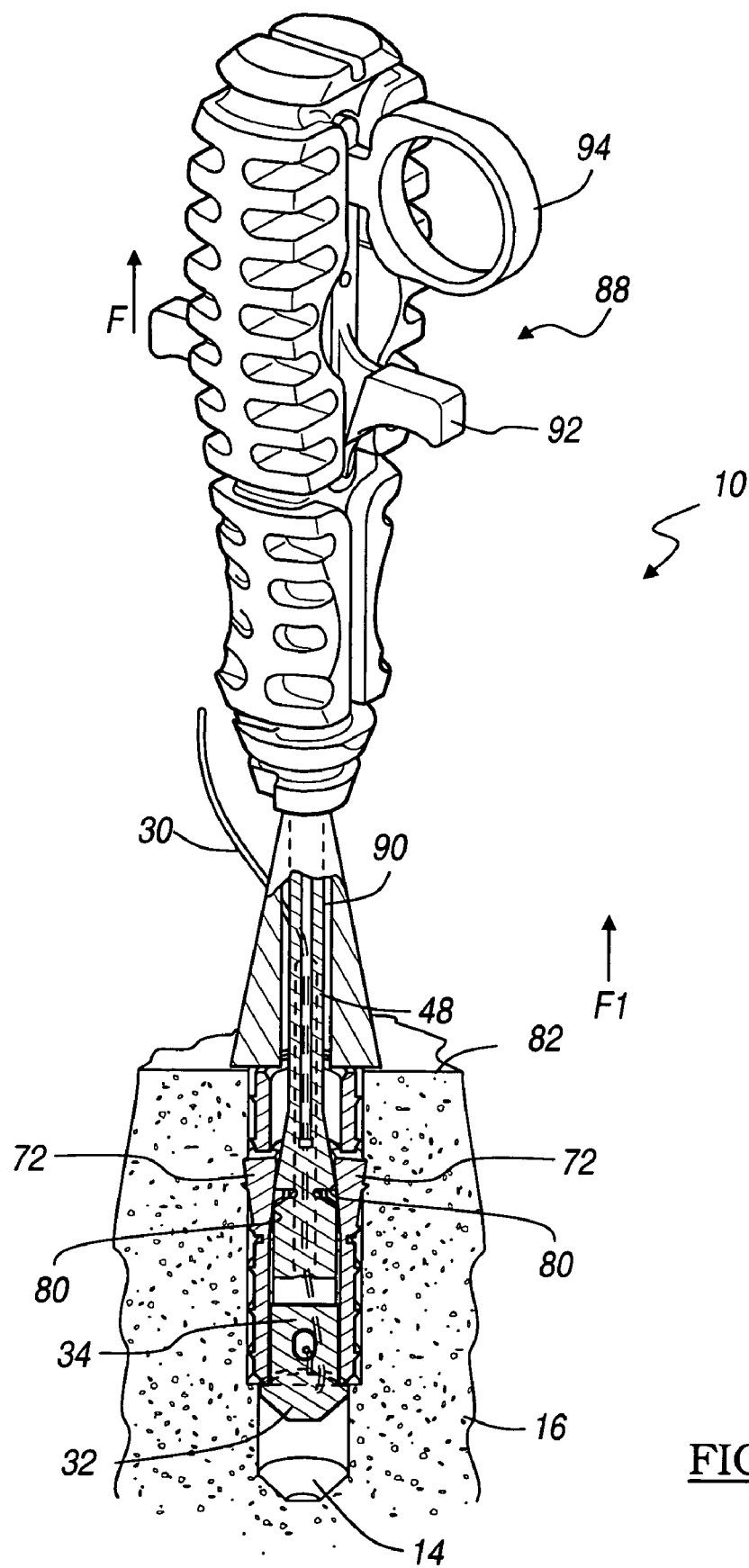
FIG. 4D is an environmental view illustrating an alternate embodiment of an actuator gun for use with the suture anchor shown in FIG. 1.

Next, the actuator gun 56 is applied to the suture anchor 10 as shown in FIGS. 4A and 4B. When a trigger 84 on the actuator gun 56 is pulled, the actuator gun 56 applies the retractive force F1 to the actuator pin 12. It should be noted, however, that the actuator gun 56 may not be the only actuating device capable of applying the retractive force F1 to the suture anchor 10. In particular, numerous other devices may be employed such as, for example, a syringe-type actuator 88 as shown in FIG. 4D. In FIG. 4D, the syringe-type actuator 88 includes a cannula 90 which engages the actuator pin 12. A lever 92 can be used to retract the cannula 90 by the application of a force F to the lever 92. More specifically, the lever 92 operates to retract the cannula 90 once it is engaged with the actuator pin 12 to provide the retractive force F1 to the suture anchor 10. A stop 94 can also be provided to prevent the lever 92 from prematurely applying the retractive force F1.

The application of the retractive force F1 causes the insert 18 to displace rearwardly with respect to the sleeve 20 as illustrated in FIG. 4B. This rearward displacement causes the tapered portion 46 to apply a force F2 to the tapered interior bearing surface 80 of the expanding members 72 of the sleeve 20. As the insert 18 continues to move rearward, the tapered portion 46 applies an increasingly greater force F2 to the tapered interior bearing surface 80 of the expanding members 72 until the expanding members 72 are engaged with the boney structure 16.

Figure 5A:
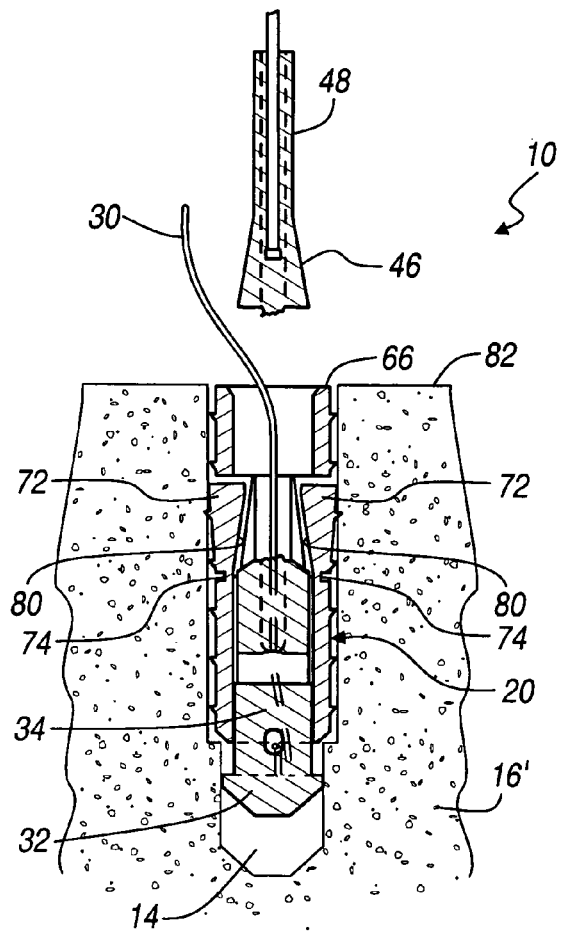
FIG. 5A is an environmental view illustrating an alternate use of the suture anchor of FIG. 1 after the application of a first retractive force.
Figure 5B:
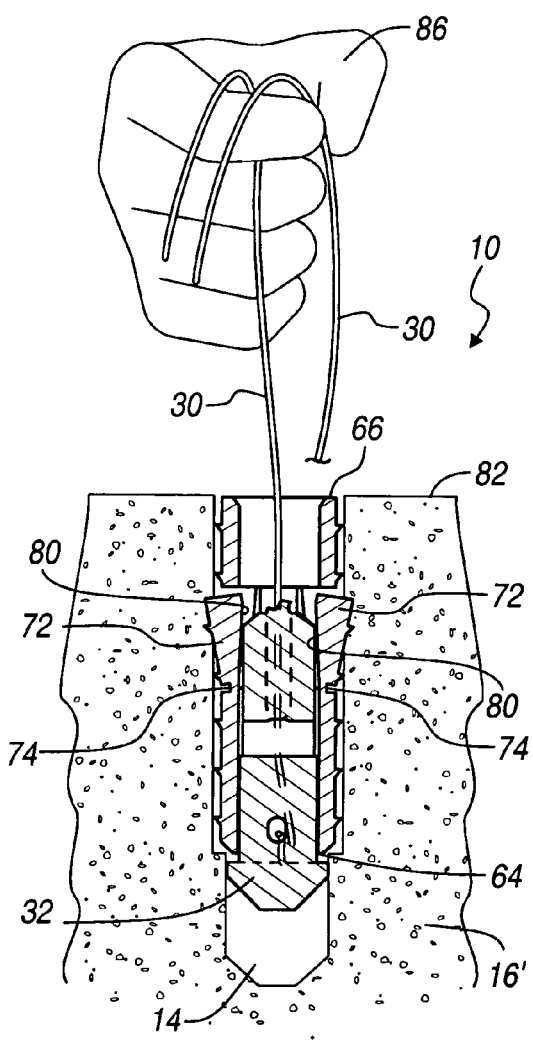
FIG. 5B is an environmental view of the suture anchor as a second retractive force is applied.

In a soft boney structure 16, when the expanding members 72 are fully engaged, the tip 32 of the suture receiving portion 22 is pressed against the first end 64 of the sleeve 20, and thus the insert 18 is not able to further retract. Hence, the continued application of the retractive force F1 causes the breakaway section 26 to fracture, as shown in FIG. 4C. With reference now to FIG. 5A, in a hard boney structure 16', however, the breakaway section 26 may fracture prior to the tip 32 of the suture receiving portion 22 contacting the first end 64 of the sleeve 20. In this situation, the suture 30 can be pulled by a hand 86 of an operator, as illustrated in FIG. 5B, such that the tip 32 of the suture receiving portion 22 abuts the first end 64 of the sleeve 20. The pulling of the suture 30 by the operator 86 causes the expanding members 72 to expand further due to the force applied to the tapered interior bearing surface 80 of the expanding members 72 by the cylindrical body 34 of the suture receiving portion 22. In either hard or soft boney structures 16, 16' once the breakaway section 26 fractures, the sleeve 20 and suture receiving portion 22 remain in the pre-drilled hole 14 to couple a selected soft tissue to the boney structures 16, 16' via the suture 30.

Figure 6A:
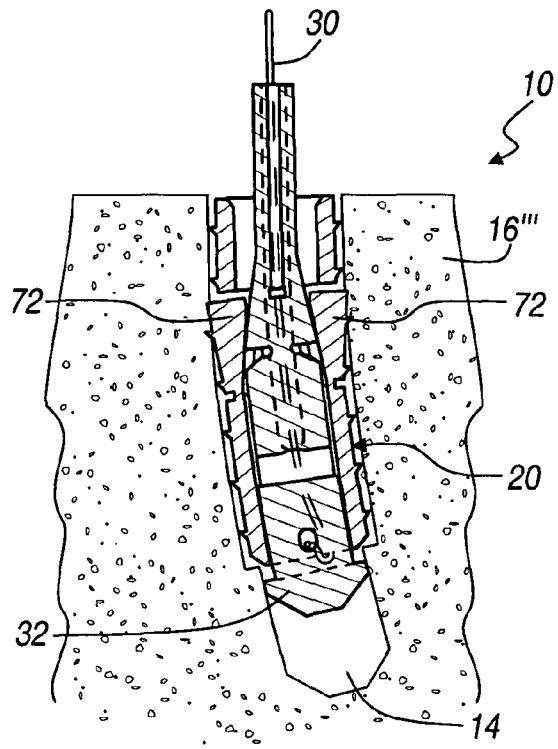
FIG. 6A is an alternate environmental view of a use of the suture anchor of FIG. 1.
Figure 6B:
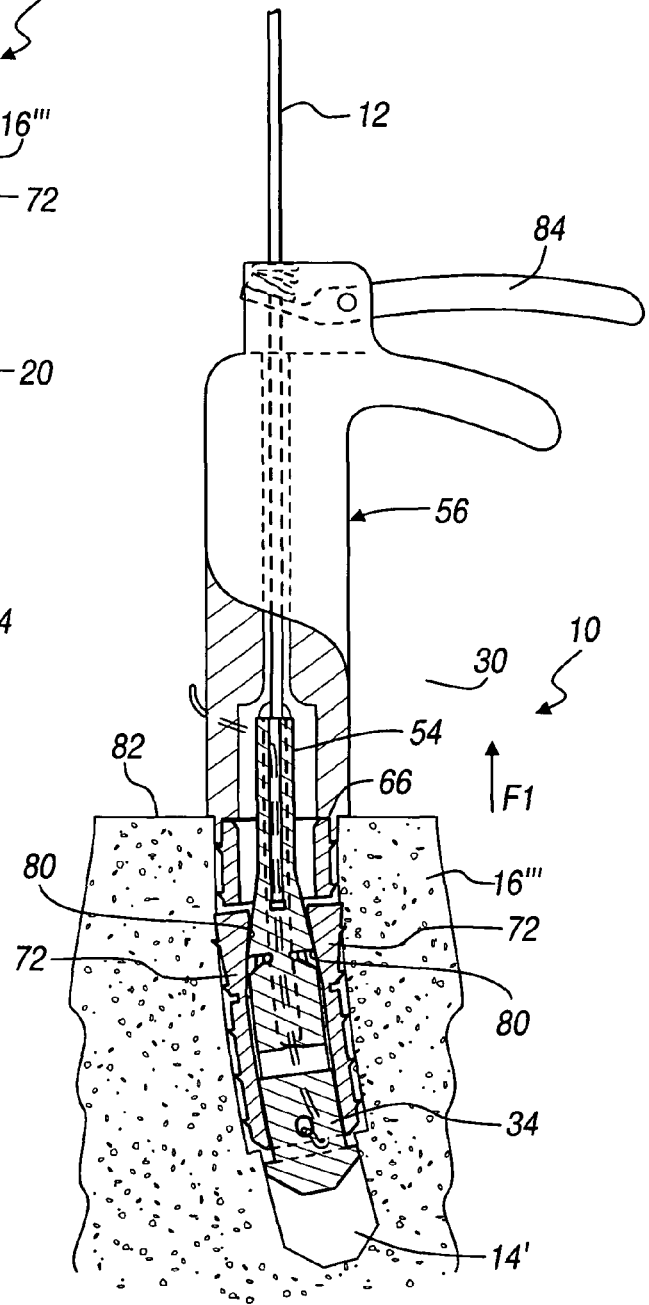
FIG. 6B is an environmental view of the suture anchor of FIG. 6A during the application of a retractive force.

In addition, the suture anchor 10 of the present invention is also adaptable for use in a curved pre-drilled hole 14' as shown in FIG. 6A. In this exemplary embodiment, the suture anchor 10 may be positioned in the curved pre-drilled hole 14' via the actuator pin 12. Next, as shown in FIG. 6B, the retractive force F1 may be applied to the actuator pin 12 by an actuating device, such as the actuator gun 56, to cause the expanding members 72 to engage the boney structure 16''' as discussed previously.

Hence, the suture anchor 10 of the present invention allows for improved soft tissue repair by ensuring the suture anchor 10 and thus the suture 30 are firmly and fixedly engaged with the boney structures 16 or 16' in the pre-drilled holes 14 and 14'. In particular, the suture anchor 10 of the present invention provides a secured attachment point for soft tissue in either soft or hard boney structures 16, 16' through the use of the actuation gun 56 or syringe-type actuator 88 in combination with the molded actuator pin 12. The ability of the suture anchor 10 to securely engage boney structures 16, 16' ensures the soft tissue is held close to the bone for improved healing time.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A suture anchor for attaching soft tissue to a pre-selected area of a boney structure, the suture anchor comprising:

an insert including a suture receiving section having a proximal end, a distal end defining a distal tip of the insert and a suture attachment area at the distal end adjacent the distal tip, a frangible breakaway portion having one end to attached on a proximal end of the suture receiving section and an opposite end attached on a first end of a tapered section, and an annular body attached on the tapered section at a second end opposite the first end, the frangible breakaway portion having a diameter less than a diameter of the suture receiving section;

a unitary sleeve disposed around at least a portion of the insert, the sleeve including at least one hinged expanding feature defined by at least one slot formed at a midsection of the sleeve and contained within the sleeve so as to be spaced apart from respective ends of the sleeve, wherein the at least one hinged expanding feature is operable to radially expand and engage the boney structure to retain the insert in the boney structure while a diameter of the sleeve between the at least one hinged expanding feature and each respective end of the sleeve remains substantially unchanged; and an actuator pin secured to the insert, wherein the actuator pin is operable to move the tapered section relative to the sleeve to engage the sleeve via the at least one hinged expanding feature with the boney structure.

2. The suture anchor of claim 1 wherein the tapered section of the insert includes a conical shape and is molded to the actuator pin.

3. The suture anchor of claim 1 wherein the attachment area of the suture receiving section defines an eyelet for receipt of a suture operable to retain the soft tissue.

4. The suture anchor of claim 1 wherein the insert is made of a resorbable material.

5. The suture anchor of claim 1 wherein the sleeve further includes:

an inner bore defining a tapered portion; and wherein the at least one hinged expanding feature is coupled to the tapered portion and is disposed adjacent to the breakaway portion of the insert, and wherein the inner bore includes an uninterrupted annular surface at the respective ends of the sleeve.

6. The suture anchor of claim 5 wherein the at least one expanding feature is activated by applying a retractive force to the actuator pin, the retractive force causing the breakaway portion and the tapered section to separate from the insert when the breakaway portion is adjacent to the tapered portion of the sleeve.

7. The suture anchor of claim 6 wherein the retractive force is applied via an actuator device.

8. The suture anchor of claim 6 wherein the retractive force causes the insert to be displaced in the sleeve whereby the displacement of the insert causes the tapered section of the insert to contact the tapered portion of the sleeve to force the hinged expanding feature to expand.

9. The suture anchor of claim 1 wherein the sleeve is made of a resorbable material.

10. The suture anchor of claim 1 wherein the actuator pin is made from a biocompatible corrosive resistant metal.

11. The suture anchor of claim 1 wherein the actuator pin is molded into the insert.

12. The suture anchor of claim 3, wherein the eyelet fixedly retains the suture in the boney structure without requiring knotting of the suture.

13. The suture anchor of claim 1, wherein the at least one expanding feature includes two expanding features formed about 180 degrees apart at the midsection of the sleeve.

14. The suture anchor of claim 1, wherein the at least one expanding feature includes a tapered interior bearing surface, and the relative movement of the insert by the actuator pin causes the insert to contact the tapered interior surface of the at least one expanding feature to cause the at least one expanding feature to engage the anatomy.

15. The suture anchor of claim 13, wherein the two expanding features are spaced apart by a distance substantially equal to an outer diameter of the annular body.

16. The suture anchor of claim 1, wherein the actuator pin includes a distal end directly attached to the tapered section, the metallic member extending through the annular body such that a proximal end of the actuator pin extends beyond a proximal end of the annular body.

17. A suture anchor for attaching soft tissue to a preselected area of a boney structure, the suture anchor comprising:
an insert that includes a suture receiving section defining an eyelet at a distal end thereof for receipt of a suture to retain the soft tissue, a breakaway portion attached directly to the suture receiving section at a proximal end thereof, a tapered section attached directly to an opposite end of the breakaway portion at a first end of the tapered section, and an elongated annular body attached directly to a second end of the tapered section, a diameter of the first end of the tapered section having a diameter greater than a diameter of the second end of the tapered section and a diameter of the annular body, the breakaway portion having a diameter smaller than the first end of the tapered section;
a sleeve slideably engaged with the insert and including a hinged expanding feature coupled to a midsection of the sleeve, the sleeve defining a throughbore including a tapered area coupled to the hinged expanding feature;
an actuator pin attached to the tapered section and annular body of the insert; and
wherein the application of force to the actuator pin causes the insert to slide and the tapered section to contact the tapered area of the sleeve to radially expand and engage the hinged expanding feature with the boney structure while a diameter of non-tapered portions of the sleeve between the tapered area and each respective end of the sleeve remains substantially unchanged.

18. The suture anchor of claim 17 wherein the sleeve is disposed around the suture receiving section, breakaway section and tapered section.

19. The suture anchor of claim 17 wherein the tapered section of the insert is molded to the actuator pin, and wherein the actuator pin extends through the annular body such that a proximal end of the actuator pin extends beyond a proximal end of the annular body.

20. The suture anchor of claim 17 wherein the hinged expanding feature is disposed adjacent to the breakaway portion of the insert and is defined by a U-shaped slot formed at the midsection of the sleeve.

21. The suture anchor of claim 17 wherein the hinged expanding feature is activated by the application of force to the actuator pin, the force operable to cause the insert to be displaced in the sleeve whereby the displacement of the insert causes the tapered section of the insert to contact the tapered area of the sleeve to force the expanding feature to expand and the breakaway portion to separate from the insert.

22. The suture anchor of claim 21 wherein the force is applied to the actuator pin via an actuation device.

23. The suture anchor of claim 21 wherein the force is applied to the actuator pin via an actuation device and a second force is applied by an operator to the suture.

24. The suture anchor of claim 17, wherein application of force to the actuator pin causes the breakaway portion and the tapered section to detach from the insert upon full engagement of the hinged expanding feature with the boney structure.

25. A suture anchor for attaching soft tissue to a preselected area of a boney structure, the suture anchor comprising:
a unitary sleeve including an expanding member that engages the boney structure, the expanding member hingedly coupled to a midsection of the sleeve and defined by a slot contained within the midsection of the sleeve such that the slot is spaced apart from respective ends of the sleeve;
an insert that retains the soft tissue, the insert including:
a suture receiving section having an aperture at a distal end adjacent a distal tip of the insert that receives a suture that retains the soft tissue;
a frangible breakaway portion having one end attached on a proximal end of the suture receiving section opposite the distal tip;
a tapered section having a first end attached on an end of the frangible breakaway portion opposite the end attached to the suture receiving section; and
an annular body attached on a second end of the tapered section opposite the first end;
wherein the sleeve is disposed around at least a portion of the insert and the frangible breakaway portion includes a diameter smaller than a diameter of the tapered section first end;
an actuating member disposed around the insert that is operable to cause the tapered section to expand the expanding member to engage the boney structure while a diameter of the sleeve between the expanding member and each respective end of the sleeve remains substantially unchanged, the actuating member including a metallic member molded to the tapered section of the insert and received through the annular body of the insert so that the metallic member extends beyond the expanding member.

26. The suture anchor of claim 1 wherein the sleeve further includes:
an inner bore defining a tapered section, wherein the expanding member is coupled to the tapered section of the sleeve and disposed adjacent to the breakaway portion of the insert.

27. The suture anchor of claim 26 wherein the expanding member is activated by applying a retractive force to the actuating member, the retractive force operable to cause the breakaway portion and the insert tapered section to separate from the insert when the breakaway portion is adjacent to the tapered section of the sleeve.

28. The suture anchor of claim 27 wherein the retractive force is applied via an actuating device coupled to the metallic member of the actuating member.

29. The suture anchor of claim 27 wherein the retractive force causes the insert to be displaced in the sleeve whereby the displacement of the insert causes the tapered section of the insert to contact the tapered section of the sleeve to force the expanding member to expand.

30. The suture anchor of claim 1, wherein the aperture of the suture receiving section fixedly secures the suture to the boney structure without the use of a knot.

31. The suture anchor of claim 26, further comprising the inner bore defining a pair of tapered sections formed approximately 180 degrees apart, wherein the pair of tapered sections are spaced apart by a distance substantially equal to an outer diameter of the annular body.

32. The suture anchor of claim 1, wherein the metallic member includes a distal end directly attached to the tapered section, the metallic member extending through the annular body such that a proximal end of the metallic member extends beyond a proximal end of the annular body.

33. An expandable suture anchor for attaching a suture to a pre-selected area of a boney structure, the suture anchor comprising:

- an insert operable to retain the suture, the insert including a suture receiving section separated from an end section by a frangible breakaway section, the suture receiving section including a proximal end and a distal end defining a distal tip and the end section including a tapered portion, the frangible breakaway section having one end directly attached to the proximal end of the suture receiving section and an opposite end directly attached to a distal end of the tapered portion, the frangible breakaway section having a diameter smaller than a diameter of the suture receiving section;
- a sleeve disposed around a portion of the insert including the frangible breakaway section and the tapered portion, the sleeve including at least one hinged expanding feature coupled to a midsection of the sleeve and adjacent to the tapered portion of the insert, the sleeve including an inner bore defining a tapered area coupled to the at least one hinged expanding feature, the sleeve being operable via the at least one hinged expanding feature to engage the boney structure to retain the insert in the boney structure; and
- an actuator pin fixedly attached to the end section of the insert, the actuator pin operable to cause the tapered portion of the insert to engage the tapered area of the sleeve to fully expand the at least one hinged expanding feature to engage the boney structure while a diameter of the sleeve between the at least one hinged expanding feature and each respective end of the sleeve remains substantially unchanged;
- wherein upon full engagement of the at least one hinged expanding feature with the boney structure, the frangible breakaway section of the insert fractures and the end section of the insert is detached from the suture receiving section.

34. The suture anchor of claim 33 wherein the at least one hinged expanding feature is activated by applying a retractive force to the actuator pin.

* * * * *

UNITED STATES PATENT AND TRADEMARK OFFICE
CERTIFICATE OF CORRECTION

| | | |
|---|---|---|
| PATENT NO. | : 7,976,565 B1 | Page 1 of 1 |
| APPLICATION NO. | : 11/006398 | |
| DATED | : July 12, 2011 | |
| INVENTOR(S) | : Jason D. Meridew | |

It is certified that error appears in the above-identified patent and that said Letters Patent is hereby corrected as shown below:

Column 1,
Line 66, replace --breakaway-- with --break away--

Column 2,
Line 53, replace --discussions-- with --discussion--

Column 4,
Line 4, replace --through out-- with --throughout--

Column 4,
Line 34, after "understood" insert --that--

Column 6,
Line 5, Claim 1, replace --end to attached-- with --end attached--

Signed and Sealed this
Twenty-ninth Day of November, 2011

David J. Kappos
*Director of the United States Patent and Trademark Office*